(12) United States Patent
Choi

(10) Patent No.: US 12,399,171 B2
(45) Date of Patent: Aug. 26, 2025

(54) MICROCHIP AND DEVICE FOR QUANTITATIVE ANALYSIS OF ANTIGEN, AND METHOD FOR QUANTITATIVE ANALYSIS OF ANTIGEN USING SAME

(71) Applicant: SMALL MACHINES, Daejeon (KR)

(72) Inventor: Jun Kyu Choi, Seoul (KR)

(73) Assignee: SMALL MACHINES, Seoul (KR)

( * ) Notice: Subject to any disclaimer, the term of this patent is extended or adjusted under 35 U.S.C. 154(b) by 499 days.

(21) Appl. No.: 16/762,662

(22) PCT Filed: Nov. 9, 2017

(86) PCT No.: PCT/KR2017/012678
§ 371 (c)(1),
(2) Date: May 8, 2020

(87) PCT Pub. No.: WO2019/093542
PCT Pub. Date: May 16, 2019

(65) Prior Publication Data
US 2020/0278348 A1 Sep. 3, 2020

(51) Int. Cl.
*G01N 33/543* (2006.01)
*B01L 3/00* (2006.01)

(52) U.S. Cl.
CPC ........ *G01N 33/54326* (2013.01); *B01L 3/502* (2013.01); *B01L 2300/0627* (2013.01);
(Continued)

(58) Field of Classification Search
CPC .................. G01N 33/53; G01N 33/543; G01N 33/54326; G01N 33/54333;
(Continued)

(56) References Cited

U.S. PATENT DOCUMENTS

2004/0009614 A1 1/2004 Ahn et al.
2005/0047968 A1* 3/2005 Kido ................ B01L 3/502753
422/400

(Continued)

FOREIGN PATENT DOCUMENTS

KR 10-2006-0094416 A 8/2006
KR 10-2014-0098285 A 8/2014

OTHER PUBLICATIONS

Tekin Cumhur, et al., "Ultrasensitive Protein Detection: A Case For Microfluidic Magnetic Bead-Based Assays", The Royal Society of Chemistry, 2013, vol. 13, pp. 4711-4739.
(Continued)

*Primary Examiner* — Christopher L Chin
(74) *Attorney, Agent, or Firm* — Sughrue Mion, PLLC

(57) ABSTRACT

The present invention provides a method of quantitatively analyzing an antigen, the method comprising: a step of mixing an assay sample comprising a target antigen, magnetic particles on which a first antibody subjected to an antigen-antibody reaction with the target antigen is immobilized, and beads on which a second antibody different from the first antibody is immobilized; a step of adding dropwise the mixed assay sample to a microchip for quantitatively analyzing an antigen; a step of introducing the microchip into a digital inline microscope-based detector comprising a magnetic force applicator and applying magnetism to the magnetic force applicator; and a step of detecting the beads using images acquired in the detector to count the number of the target antigens.

8 Claims, 13 Drawing Sheets

(52) U.S. Cl.
CPC .............. *B01L 2300/0681* (2013.01); *B01L 2300/0819* (2013.01); *B01L 2400/043* (2013.01)

(58) Field of Classification Search
CPC ............ G01N 33/54366; G01N 15/14; G01N 2015/0019; G01N 15/0612; G01N 15/1436; G01N 2021/1765; G01N 2021/178; G01N 2203/0647; G01N 2223/401; G01N 2223/402; G01N 2223/413; G01N 2021/5957; G01N 35/0098; G01N 21/62; B01L 3/502; B01L 3/502715; B01L 3/502761; B01L 2300/0627; B01L 2300/0681; B01L 2300/0819; B01L 2300/0893; B01L 2400/043; B01L 2200/0668
USPC ............. 422/82.05, 407, 503; 436/526, 534; 356/948
See application file for complete search history.

(56) References Cited

U.S. PATENT DOCUMENTS

| | | | | |
|---|---|---|---|---|
| 2011/0065209 | A1* | 3/2011 | Heil | G01N 33/54326 422/69 |
| 2016/0216208 | A1* | 7/2016 | Kim | H04N 23/45 |
| 2018/0095067 | A1* | 4/2018 | Huff | G01N 33/48721 |
| 2018/0327827 | A1* | 11/2018 | Han | C12N 15/115 |

OTHER PUBLICATIONS

Korean Office Action of KR 10-2018-7024087 dated Sep. 25, 2019.
International Search Report for PCT/KR2017/012678 dated May 2, 2018 [PCT/ISA/210].
Written Opinion for PCT/KR2017/012678 dated May 2, 2018 [PCT/ISA/237].

* cited by examiner

MICROCHIP AND DEVICE FOR QUANTITATIVE ANALYSIS OF ANTIGEN, AND METHOD FOR QUANTITATIVE ANALYSIS OF ANTIGEN USING SAME

CROSS REFERENCE TO RELATED APPLICATIONS

This application is a National Stage of International Application No. PCT/KR2017/012678 filed Nov. 9, 2017.

TECHNICAL FIELD

The present invention relates to a microchip for quantitatively analyzing an antigen which includes channels configured to facilitate detection of a target antigen present in an assay sample; a device for quantitatively analyzing an antigen which is configured to count a target antigen detected in the microchip to quantitatively analyze the target antigen; and a method of detecting a target antigen using the microchip and the device.

BACKGROUND ART

An antigen analysis method is a method of diagnosing diseases caused by viral infections. In particular, an antigen analysis method induces an immune response using an antibody that recognizes an antigen derived from viruses, thereby detecting a target antigen and, thus, diagnosing diseases mediated by viruses. With regard to accurate diagnosis of diseases and monitoring of therapeutic effects, qualitative analysis of the presence or absence of antigens such as viruses, as well as quantitative analysis of an antigen to measure the amount of antigen present in a target sample, may be important.

Meanwhile, with the development of miniaturized analytical microchips, to which the lab-on-a-chip technology is applied, and diagnostic methods using the same, quantitative analysis of an antigen in a target sample can be performed more rapidly. As a probe, e.g., an antibody specific for a target substance such as an antigen, is immobilized on inner walls of microchannels in such a microchip, target substances suspended in the channels can be detected. Here, since the probe is fluorescently labeled, a target material detected on a microchip may be quantitatively analyzed by detecting fluorescence quantity, light emission quantity, light absorbance quantity, or scattered light quantity of a chemically treated target material and quantifying average intensities of the detected signals.

However, in a microchip in which a main driving force that causes the movement of an assay sample is capillary force, action force due to interaction between upper and lower inner walls of microchannels and a fluid may be different from action force due to interaction between left and right inner walls of the microchannels and the fluid. Accordingly, an assay sample flowing through spaces formed by the channels may have an irregular and nonuniform movement pattern. The movement pattern of the assay sample may cause a decrease in the efficiency of an antigen-antibody reaction between an antigen in the assay sample and an antibody immobilized on channels and, further, a decrease in the sensitivity of detection of immune complexes formed by the antigen-antibody reaction. Accordingly, when a small amount of antigen is present in an assay sample, the quantitative analysis result thereof is less reliable.

In addition, in the method of quantitatively analyzing a detected antigen by quantifying the average intensity of signals detected on a microchip, the precision of estimated values may differ depending on the sensitivity of a detection sensor, so that sensitive sensor calibration may be required to maintain the accuracy. As a result, new problems such as complexity of a circuit and cost increase may be caused. In addition, in the case of the quantitative analysis method, signals derived from a fluorescently labeled probe not bound to an antigen in channels, or fluorescence probe-target antigen complexes bound to a target antigen, but floating without being immobilized in the chip may cause errors.

Therefore, to precisely diagnose a disease using microchips and, further, to monitor treatments, there is a need for development of a novel method of quantitatively analyzing an antigen which is capable of providing improved sensitivity to detection of disease-specific antigens.

The background art of the invention has been described to facilitate understanding of the present invention. It should not be understood that the matters described in the background form as prior art of the present invention.

DISCLOSURE

Technical Problem

The present inventors have recognized that problems of existing antigen analysis methods can be addressed by using beads having magnetism, excluding an optical label, and a countable size for quantitative antigen analysis.

As a result, the present inventors have developed a novel method of quantitatively analyzing an antigen which is characterized by using magnetic particles and beads with a countable size that form immune complexes via a target antigen.

In particular, the present inventors have developed a fluid drag and magnetism-based microchip for quantitatively analyzing an antigen to highly, sensitively detect immune complexes formed by an antigen-antibody reaction between a target antigen, magnetic particles and beads, wherein the fluid drag and magnetism-based microchip includes channels in which wells are formed. Further, the present inventors have determined the size of beads that can move while rotating on one surface of a channel and are optically countable. In addition, the present inventors have developed a digital inline microscope-based device for quantitatively analyzing an antigen which is configured such that immune complexes can be effectively captured in wells formed in the microchip through application of magnetism and beads of the immune complexes captured in the microchip can be optically counted in a wide analysis range to provide rapid and highly accurate quantitative analysis for an antigen.

Therefore, the present invention has been made in view of the above problems, and it is one object of the present invention to provide a method of quantitatively analyzing an antigen which can provide highly accurate quantitative analysis for an antigen in an assay sample by using a fluid drag and magnetism-based microchip for quantitatively analyzing an antigen and a digital inline microscope-based device for quantitatively analyzing an antigen.

It is another object of the present invention to provide a microchip for quantitatively analyzing an antigen which is characterized by flowing an assay sample based on fluid drag and magnetism and being capable of effectively capturing an antigen due to wells included therein and, thus, facilitating quantitative analysis therefor.

It is yet another object of the present invention to provide a digital inline microscope-based device for quantitatively analyzing an antigen which can provide rapid analysis due to a wide analysis range and effectively count antigens detected in a microchip excluding a fluorescence-labeled material.

It will be understood that technical problems of the present invention are not limited to the aforementioned problems and other technical problems not referred to herein will be clearly understood by those skilled in the art from disclosures below.

Advantageous Effects

As apparent from the above description, a trace amount of antigen in an assay sample can be detected by immunoreacting magnetic particles and beads, to which different monoclonal antibodies are respectively attached, with the same target antigen.

In addition, since the present invention provides beads having an optically countable size, a microchip and device for quantitatively analyzing an antigen which is capable of providing optical quantitative analysis for an antigen without use of a fluorescently labeled probe; and a method of quantitatively analyzing an antigen using the microchip and the device can be provided.

Further, since the present invention uses fluid drag and magnetism, drawbacks of existing microchips using capillary force as a main driving force can be addressed. Accordingly, the present invention can provide a microchip and device for quantitatively analyzing an antigen which have high detection sensitivity for immune complexes formed by an antigen-antibody reaction; and a method of quantitatively analyzing an antigen using the microchip and the device.

In particular, in the case of the microchip for quantitatively analyzing an antigen including channels in which wells are formed, immune complexes including magnetic particles can be effectively captured in the microchip as magnetism is applied. Further, aggregated immune complexes can be separated from each other by the wells. As a result, one immune complex may be captured in one well. Accordingly, the present invention can highly accurately detect target antigens floating in a microchip and can allow easy optical analysis for immobilized target antigens.

In addition, the present invention can provide simultaneous antigen analysis tests for a plurality of target antigens by adjusting the sizes, shapes, and the like of beads for the plurality of target antigens to provide different complex shapes and, thus, adjusting the size of wells in the microchip.

Further, the present invention three-dimensionally utilizes particles that play two different roles to use immune complexes wherein an antibody is immobilized on a larger surface area relative to a volume, thereby being capable of increasing the efficiency of immune response. Accordingly, the present invention can effectively detect a target antigen and target substance at low concentrations.

Effects according to the present invention are not limited by those exemplified above, and more various effects are included in the present specification.

MODES OF THE INVENTION

Figure 1:
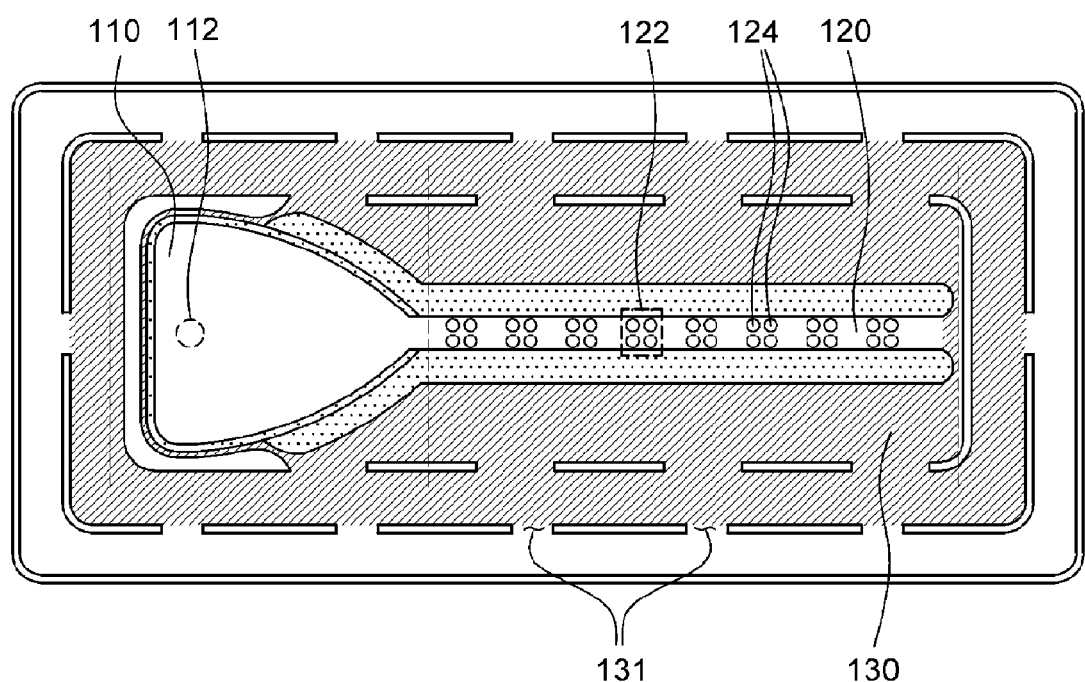
FIG. 1 illustrates a schematic plan view of a microchip for quantitatively analyzing an antigen according to an embodiment of the present invention.

The attached drawings for illustrating exemplary embodiments of the present invention are referred to in order to gain a sufficient understanding of the present invention, the merits thereof, and the objectives accomplished by the implementation of the present invention. The invention may, however, be embodied in many different forms for detecting an antigen through an immune reaction and should not be construed as being limited to the embodiments set forth herein; rather, these embodiments are provided so that this disclosure will be thorough and complete, and will fully convey the concept of the invention to one of ordinary skill in the art. Meanwhile, the terminology used herein is for the purpose of describing particular embodiments and is not intended to limit the invention.

The shapes, sizes, ratios, angles, numbers, and the like disclosed in drawings for describing embodiments of the present invention are exemplary, and thus, the present invention is not limited to the illustrated particulars. In addition, in the following description of the present invention, a detailed description of known functions and configurations incorporated herein will be omitted when it may make the subject matter of the present invention unclear. In expressions "comprise", "have", "consist of" and the like mentioned in the present specification, other parts may be added unless 'only' is used. Singular forms "a," "an" and "the" are intended to include the plural forms as well, unless the context clearly indicates otherwise.

In interpreting components, it is interpreted to include error ranges even if there is no separate description.

Each of the features of the various embodiments of the present invention may be combined with each other in part or in whole, various interlocking and driving are allowed as can be understood by those skilled in the art, and each of embodiments may be implemented independently or together in combined forms.

For clarity of interpretation of the present specification, the terms used herein will be defined below.

The term "quantitative analysis" used in the present specification refers to an assay that clarifies a quantitative relationship that constitutes a substance. According to various embodiments of the present invention, a method of quantitating an antigen is provided. For example, in accordance with the method of quantitating an antigen using the microchip and device for quantitively analyzing an antigen according to an embodiment of the present invention, a target antigen may be detected and quantitatively analyzed by counting immune complexes captured in the detection channel. Quantitative analysis of a target antigen such as a disease-specific antigen may be important in providing precise diagnosis of a disease and monitoring the therapeutic effect of the disease.

Here, the microchip for quantitatively analyzing an antigen according to an embodiment of the present invention may be used for quantitative analysis of an antigen.

In particular, inside a microchip for quantitatively analyzing an antigen, channels, in which fluid communicates, may be formed by a body constituted of an upper surface and a lower surface.

Here, the term "channels" used in the present specification may refer to microchannels formed between an upper surface and lower surface of a body. The microchip for quantitatively analyzing an antigen according to an embodiment of the present invention includes a plurality of channels. The channels may be divided into and designated as an input channel and a detection channel according to functions thereof. For example, an input channel may be a channel into which an assay sample is introduced, and a detection channel may be a channel in which a target antigen in an assay sample is captured. Here, the detection channel may include a plurality of wells. Optionally, the channels may be referred to as a single channel which through fluid communicates.

Meanwhile, in the microchip for quantitatively analyzing an antigen, a channel height corresponding to a length from an upper surface to a lower surface may be 1 μm to 200 μm. For example, when the height of input and detection channels is 1 μm to 200 μm, turbulent laminar flow blurring with a Reynolds constant of $10^6$ or less may occur, so that a fluid-type assay sample may flow in the channels.

The term "assay sample" used in the present specification may refer to a sample including a target antigen. Preferably, an assay sample may be a fluid sample. For example, an assay sample may be a cell sample such as a cell lysate, whole blood, plasma, serum, saliva, ocular fluid, cerebrospinal fluid, sweat, urine, milk, ascites fluid, synovial fluid and peritoneal fluid, but the present invention is not limited thereto. Further, a target antigen may be an antigen or a nuclear protein that acts as an antigen. However, the target antigen may be easily selected by a user according to a purpose. Further, "assay sample" in the specification may refer to any sample introduced into a microchip for quantitatively analyzing an antigen according to an embodiment for quantitative analysis.

Meanwhile, an assay sample may be pretreated, depending upon the type thereof, before being introduced into the microchip for quantitatively analyzing an antigen according to an embodiment of the present invention. For example, an assay sample including cells may be lysed.

Further, an antigen-antibody reaction may be previously induced before introducing an assay sample into the microchip for quantitatively analyzing an antigen. For example, in the method of quantitatively analyzing an antigen according to an embodiment of the present invention, an assay sample may be subjected to an immune reaction with magnetic particles and beads to which an antibody is attached, and then may be fed into the microchip for quantitatively analyzing an antigen for quantitative analysis.

The term "antigen" used in the specification refers to a substance that reacts with an antibody causing an immune response. For example, an antigen may be a target antigen to be detected by the method of quantitatively analyzing an antigen according to an embodiment of the present invention. Further, when it is desired to identify infection by a specific virus, an antigen may be a nuclear protein of a virus. However, examples of an antigen are not limited to the aforementioned particulars, and the antigen may be any substance in an assay sample, such as cells causing an immune response, viruses, or surface molecules of protozoans, capable of immunoreacting with a specific antibody.

For example, when a respiratory infectious disease test is performed using the method of quantitatively analyzing an antigen according to an embodiment of the present invention, a target antigen may be influenza A, influenza B, respiratory syncytial virus (RSV), parainfluenza virus-1, parainfluenza virus-2, parainfluenza virus-3, adenovirus, human metapneumovirus (hMPV) or rhinovirus (1, 2). In addition, when an allergy disease test is performed using the method of quantitatively analyzing an antigen, a target antigen may be IL-1 beta, IL-10, IL-2, IL-4, IL-5, IL-6, IL-71, IFN gamma, TNF-α or GM-CSF. Further, when an acute myocardial infarction diagnostic test is performed using the method of quantitatively analyzing an antigen according to an embodiment of the present invention, a target antigen may be troponin I, BNP, high-sensitivity (hs) CRP, CK-MB, D-dimer, or myoglobin. Furthermore, when a sexually transmitted disease test is performed using the method of quantitatively analyzing an antigen according to an embodiment of the present invention, a target antigen may be human immunodeficiency virus (HIV), chlamydia bacteria, *Treponema pallidum, gonococcus* (*Neisseria gonorrhoeae*), or human papilloma virus (HPV). When a prostate cancer test is performed using the method of quantitatively analyzing an antigen according to an embodiment of the present invention, a target antigen may be a prostate specific antigen (PSA). In addition, when an immunity test of a transplantation patient is performed using the method of quantitatively analyzing an antigen according to an embodiment of the present invention, a target antigen may be a BK virus or cytomegalovirus (CMV) antigen. Further, a target antigen may be a cells itself that causes an immune response.

The term "antibody" used in the present specification refers to a substance inducing a specific immune response to an antigen so as to inactivate an antigen such as virus or bacteria and fight microorganisms that have invaded the body. Further, monoclonal antibodies, which are antibodies produced by single antibody-forming cells, refer to antibodies having uniform primary structures (amino acid sequences). The term "first antibody" used in the specification refers to a monoclonal antibody constructed to bind to an epitope of a target antigen and immobilized on magnetic particles. In addition, the term "second antibody" refers to a monoclonal antibody bound to another epitope, which is different from the first antibody-bound epitope, of the same target antigen and immobilized on beads. Here, the first and second antibodies may be different from fluorescence-labeled antibodies.

Meanwhile, after respectively mixing the first and second antibodies with magnetic particles and beads, the resultant mixture may be allowed to react in a 0.05 M morpholinoethanesulfonic acid (MES) buffer solution for 15 minutes, and a binding reaction to each of the magnetic particles and beads may be induced using 2.5 mM EDC. Here, magnetic particles not bound to the first antibody may be isolated and washed using a magnet, and beads not bound to the antibody may be isolated and washed by centrifugation (25000 g, 10 minutes).

Meanwhile, the term "beads" used in the specification may refer to particles that can be observed under a microscope without a fluorescent material or dyeing. For example, beads may be polymer beads, polystyrene beads, quantum dots, gold particles, or latex beads having sizes visible under an optical microscope with magnification 200× without fluorescence or dyeing. However, beads may be variously selected according to the performance of a detector, the type of target antigen, etc., without being limited to those described above.

The term "immune complexes" used in the specification may be immune complexes formed by binding magnetic particles and beads through target antigens. Here, the immune complexes may have an asymmetric shape. Here, magnetic particles in the immune complexes may actively control the flow of a sample in a microchip, and beads in the immune complex may be responsible for signaling such that immune complexes can be counted. Such immune complexes three-dimensionally utilize particles that play two different roles to immobilize an antibody on a larger surface area relative to a volume, thereby being capable of increasing the efficiency of an immune response. Accordingly, an antigen and target substance at low concentrations may be effectively detected by the method of quantitatively analyzing an antigen according to an embodiment of the present invention using an immune complex.

In the method of quantitatively analyzing an antigen according to an embodiment of the present invention, quantitative analysis of a target antigen may be performed by counting immune complexes. More particularly, since beads in the immune complexes have an optically countable size, target antigens indirectly bound to the beads may be quantitatively analyzed by counting the beads captured in a detection channel of the microchip for quantitative analyzing an antigen. In addition, when magnetic force is applied to the detection channel, the immune complexes may move to a detection channel by magnetic particles and may be captured and immobilized in a plurality of wells formed in the detection channel. Here, the immune complexes may move to the detection channel while rotating on one surface of the microchip by magnetism. Meanwhile, since beads that do not form immune complexes do not respond to magnetism, the beads are not captured in the detection channel. In addition, magnetic particles that do not form immune complexes may be captured in the detection channel, but may not be optically counted. Accordingly, by the method of quantitatively analyzing an antigen according to an embodiment of the present invention, highly sensitive quantitative analysis for a target antigen may be performed without use of a fluorescence-labeled antibody.

In the specification, the beads that are optically countable and move while rotating on one surface of the microchip after formation of immune complexes may have a particle diameter of 0.5 to 5 μm. Further, a particle diameter of magnetic particles that cannot be optically counted may be 0.05 to 2.8 μm.

The diameter of each of wells formed in the detection channel of the microchip for quantitatively analyzing an antigen may be 1.2 to 2 times larger than the sum of the particle diameters of the bead and the magnetic particle or the diameter of each of the immune complexes formed by the beads and the magnetic particles.

A target antigen detected in the microchip for quantitatively analyzing an antigen may be effectively, quantitatively analyzed using a device for quantitatively analyzing an antigen which is based on a magnetic force applicator and a digital inline microscope. Here, the device for quantitatively analyzing an antigen may be used in the same meaning as a detector in the specification.

Here, "magnetic force applicator" may refer to any material capable of forming magnetism, outside the microchip, with magnetic particles in the microchip for quantitatively analyzing an antigen according to an embodiment of the present invention. For example, the magnetic force applicator serves to apply magnetism to one surface of the microchip for quantitatively analyzing an antigen which includes wells therein such that immune complexes in an assay sample can flow to the detection channel. Further, since immune complexes can be effectively captured in wells by the magnetic force applicator, quantitative analysis of the immune complexes may be more easily performed. As a result, a target antigen may be highly accurately detected.

The term "digital inline microscope" used in the specification may be a microscope including an image sensor configured to convert and store an image of a target substance such as an immune complex into a digital signal. Here, the digital inline microscope may be any digital inline microscope so long as asymmetric immune complexes captured in a microchip can be counted without a fluorescent material or dyeing. For example, the digital inline microscope may be a CMOS image sensor-based lensless digital inline microscope.

Meanwhile, a device for quantitatively analyzing an antigen based on the digital inline microscope may exhibit improved analysis performance compared to existing quantitative analysis devices. More particularly, since a quantitative analysis device based on an optical magnification adjustment system performs quantitative analysis for a target antigen based on some enlarged or miniaturized images of the target antigen, it takes a long time for analysis and a quantitative analysis result may be different according to a focus of the target antigen.

When a microchip for quantitatively analyzing an antigen is introduced into that device for quantitatively analyzing an antigen according to an embodiment of the present invention which is based on a digital inline microscope, images of immune complexes captured in the microchip for quantitatively analyzing an antigen may be rapidly acquired by an image sensor. A processor of a device for quantitative analysis may reconstruct acquired images into a high-resolution image and count immune complexes in the high-resolution image. As a result, an accurate counting result of target antigens may be provided.

Hereinafter, a microchip for quantitatively analyzing an antigen used in the method of quantitatively analyzing an antigen according to an embodiment of the present invention is described with reference to FIG. 1.

FIG. 1 illustrates a schematic plan view of a microchip for quantitatively analyzing an antigen according to an embodiment of the present invention. Referring to FIG. 1, a microchip 100 for quantitatively analyzing an antigen may include a plurality of channels 110 and 120 formed between upper and lower surfaces thereof. Further, a plurality of through holes 131 may be formed at sides of the microchip 100 for quantitatively analyzing an antigen such that fluid moves in one direction. In addition, the through holes 131 may maintain air pressure such that an assay sample sufficiently flows to a flow retention channel 130.

The plurality of channels include the input channel 110 and the detection channel 120. In particular, an upper surface of the input channel 110 is configured to include an inlet 112 through which an assay sample including a target antigen is injected. The detection channel 120 may include a plurality of detection parts 122 including a plurality of wells 124. The detection parts 122 may be spaced from each other at a predetermined interval in the detection channel 120. However, the present invention is not limited thereto, and an interval, region, well number, and well size of the detection parts 122 may be varied according to the type of assay sample, a use purpose of the microchip 100 for quantitatively analyzing an antigen, or the presence or absence of multiple antigen analysis.

Meanwhile, an assay sample fed into the input channel 110 may include immune complexes composed of a target antigen, magnetic particles and beads through pretreatment. Accordingly, when magnetism is applied near the detection channel 120, immune complexes may move to the detection channel 120 while rotating on one surface of the microchip 100 for quantitatively analyzing an antigen by magnetic particles. Further, immune complexes may be captured and immobilized in the plurality of wells 124 formed in the detection channel 120. Here, aggregated immune complexes may be separated by the wells 124. As a result, one immune complex may be captured in one well 124.

Beads or target antigens that do not form immune complexes do not respond to magnetism, thereby not being captured in the detection channel 120. The beads or target antigens that did not respond to an immune response may move to the flow retention channel 130 by air pressure formed by the through holes 131.

Hereinafter, a device for quantitatively analyzing an antigen used in the method of quantitatively analyzing an antigen according to an embodiment of the present invention is described with reference to FIG. 2. Here, reference numerals used in FIG. 1 are used to refer to components for convenience of description. Here, although a lensless digital inline microscope-based device including an image sensor is described as an example, the construction of the device for quantitatively analyzing an antigen is not limited thereto and may be varied so long as target antigens or asymmetric immune complexes can be optically counted.

Figure 2:
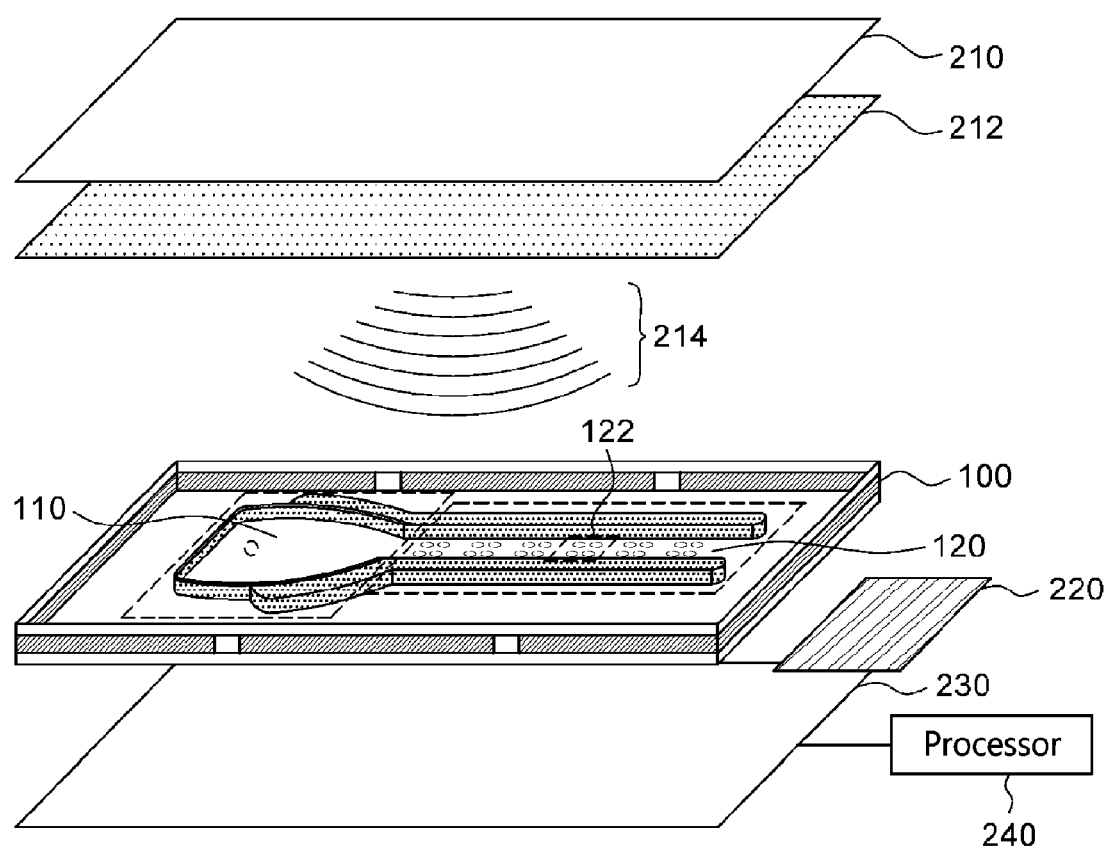
FIG. 2 illustrates a schematic exploded perspective view of a device for quantitatively analyzing an antigen according to an embodiment of the present invention.

FIG. 2 illustrates a schematic exploded perspective view of a device for quantitatively analyzing an antigen according to an embodiment of the present invention.

Referring to FIG. 2, a device for quantitatively analyzing an antigen includes a light irradiator 210, a magnetic force applicator 220, an image sensor 230, and a processor 240. Here, the microchip 100 for quantitatively analyzing an antigen in which a target antigen is detected may be disposed between the light irradiator 210 and the image sensor 230.

The light irradiator 210 may include a plurality of LEDs, and the LEDs may be configured to irradiate a specific detection part 122 of the microchip 100 for quantitatively analyzing an antigen. Here, the light irradiator 210 may include a pinhole aperture 212, and light 214 irradiated to the microchip 100 for quantitative analysis may be isotropic light. Meanwhile, the LEDs of the light irradiator 210 may be arranged at an interval of 3 mm and configured to irradiate at various angles including an angle perpendicular to the detection parts 122. For example, when the LEDs are arranged at 0° perpendicular to the detection parts 122, ±2.5°, ±3.5°, ±4.9°, ±6.9°, all of the detection parts 122 in the microchip 100 for quantitatively analyzing an antigen may be constantly irradiated with the light 214 using a small number of LEDs. As a result, high-resolution images of the detection parts 122 may be acquired. Meanwhile, the number and angles of LEDs in the light irradiator 210 may be varied according to the size and configuration of the microchip 100 for quantitatively analyzing an antigen or the type of target antigen.

The magnetic force applicator 220 is configured to apply electromagnetic force to the detection channel 120 of the microchip 100 for quantitatively analyzing an antigen. For example, the magnetic force applicator 220 may be disposed to correspond to an upper or lower surface of the microchip 100 in which the wells 124 are formed. Further, the magnetic force applicator 220 may be disposed at a position where the detection channel 120 ends such that the image sensor 230 described in detail below is not detected. Here, the magnetic force applicator 220 may have various shapes so long as magnetism is applied to the detection channel 120. When magnetism is applied near the detection channel 120 of the microchip 100 for quantitatively analyzing an antigen by the magnetic force applicator 220, immune complexes may move to the detection channel 120 while rotating on one surface of the microchip 100 for quantitatively analyzing an antigen, and may be captured and immobilized in the plurality of wells 124 formed in the detection channel 120.

The image sensor 230 may detect immune complexes captured in the plurality of wells 124 in the detection channel 120 as the light 214 is irradiated through the light irradiator 210. As a result, images of the immune complexes may be acquired. For example, a plurality of low-resolution images of immune complexes in the detection parts 122 which are generated by radiating the light 214 at a plurality of angles may be acquired by the image sensor 230. Here, the image sensor 230 may be any image sensor including a CMOS image sensor, a digital inline microscope, or a small microscope, but the present invention is not limited thereto. Meanwhile, beads forming immune complexes may have a size that can be detected by the image sensor 230, and the magnetic particles or target antigens may have small sizes that cannot be detected by the image sensor 230. For example, beads having a particle diameter of 0.5 to 5 μm may be detected by the image sensor 230, and magnetic particles having a particle diameter of 0.05 to 2.8 μm may not be detected by the image sensor 230.

The processor 240 is configured to be connected to the image sensor 230. Accordingly, based on an image acquired from the detection parts 122, immune complexes in the image may be counted. For example, the processor 240 may reconstruct a high-resolution image based on a plurality of low-resolution images of immune complexes acquired through the image sensor 230 and may count immune complexes in the high-resolution image. Accordingly, quantitative analysis of target antigens may be performed by indirectly counting the target antigen.

Hereinafter, a procedure of detecting a target antigen in the method of quantitatively analyzing an antigen according to an embodiment of the present invention is described in detail with reference to FIGS. 3A and 3B to 3E. Here, reference numerals used in FIGS. 1 and 2 are used to refer to components for convenience of description.

Figure 3A:
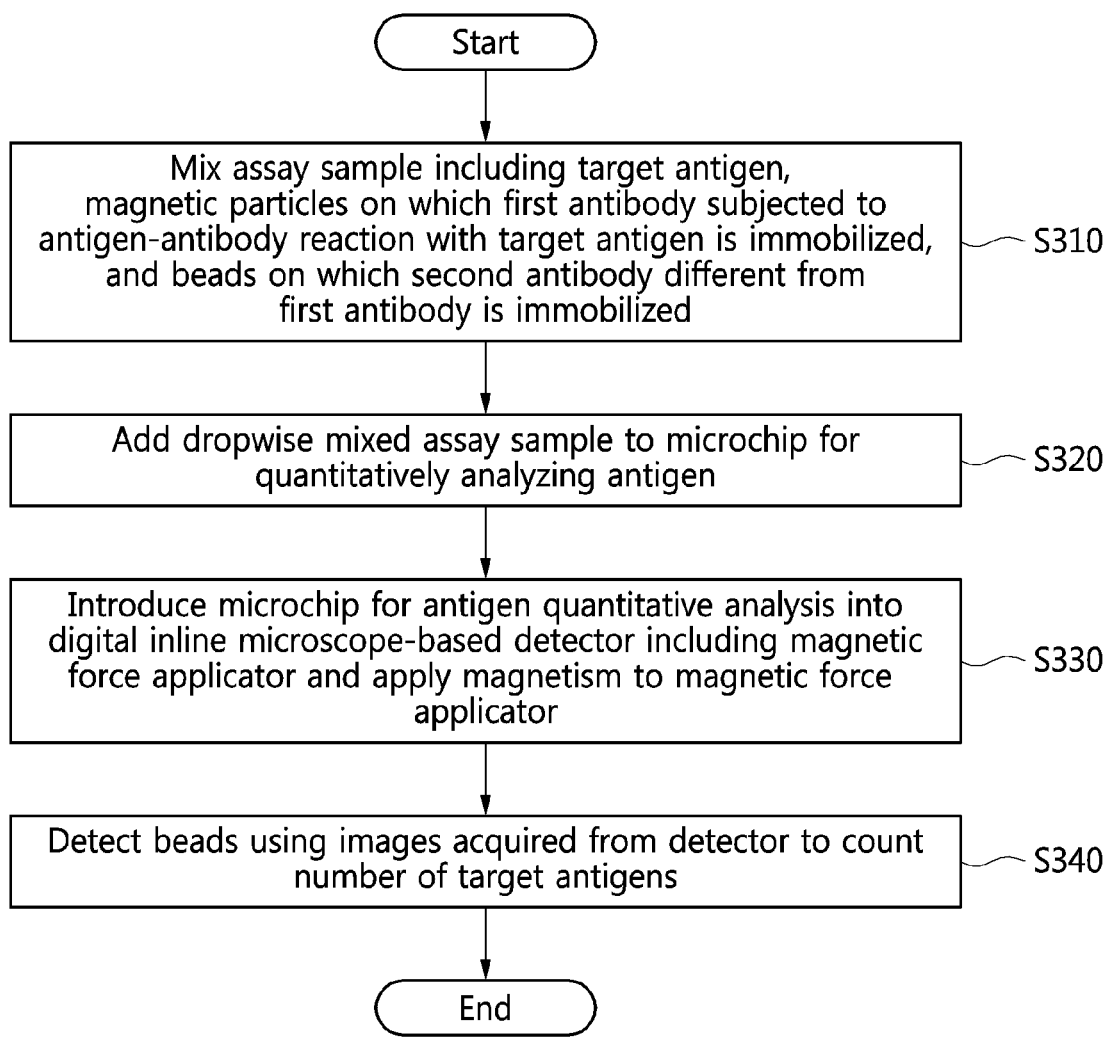
FIG. 3A illustrates a procedure of a method of quantitatively analyzing an antigen using a microchip and device for quantitatively analyzing an antigen according to an embodiment of the present invention.
Figure 3B:
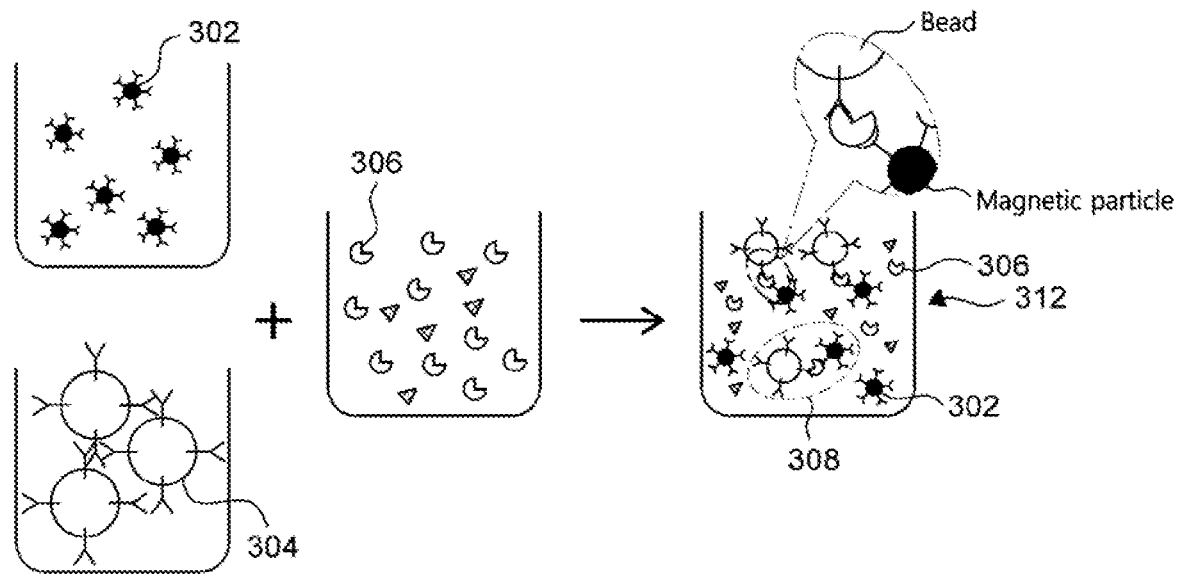
FIG. 3B exemplarily illustrates a step of mixing an assay sample, magnetic particles, and beads in a method of quantitatively analyzing an antigen.
Figure 3C:
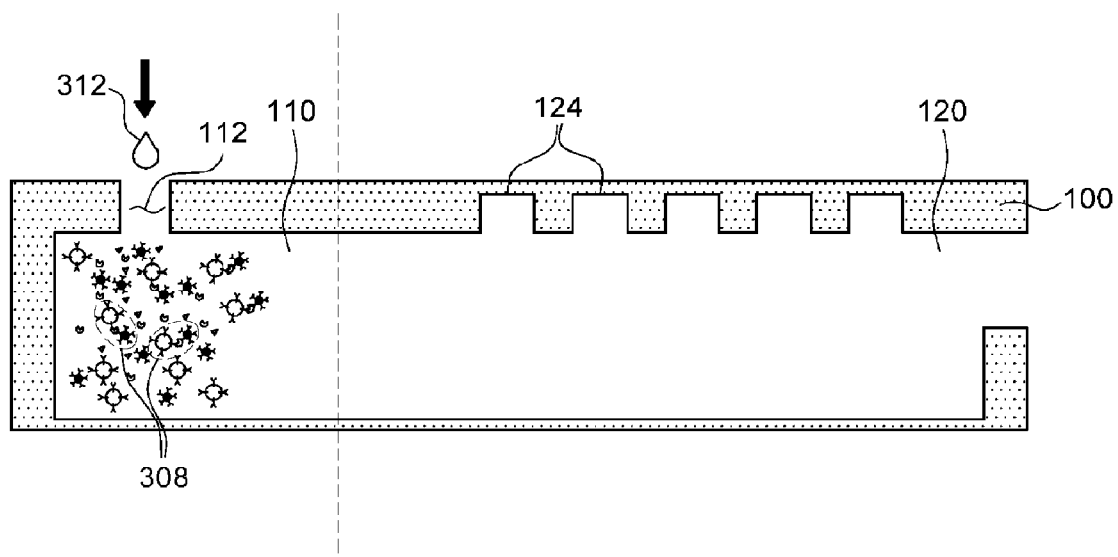
FIGS. 3C and 3D illustrate a schematic side view of a microchip for quantitatively analyzing an antigen according to an embodiment of the present invention and an enlarged view of a main part to describe a process of detecting a target antigen.
Figure 3D:
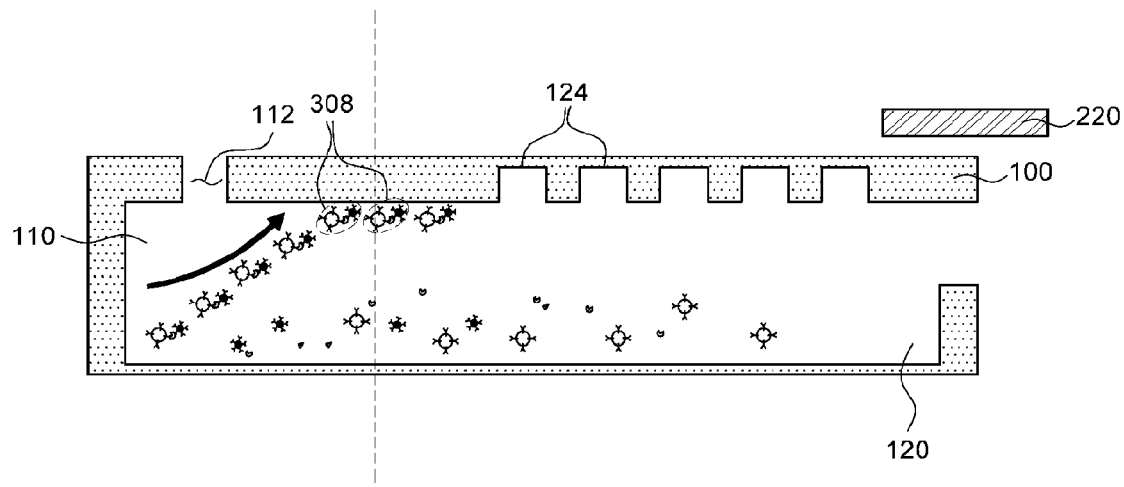
Figure 3E:
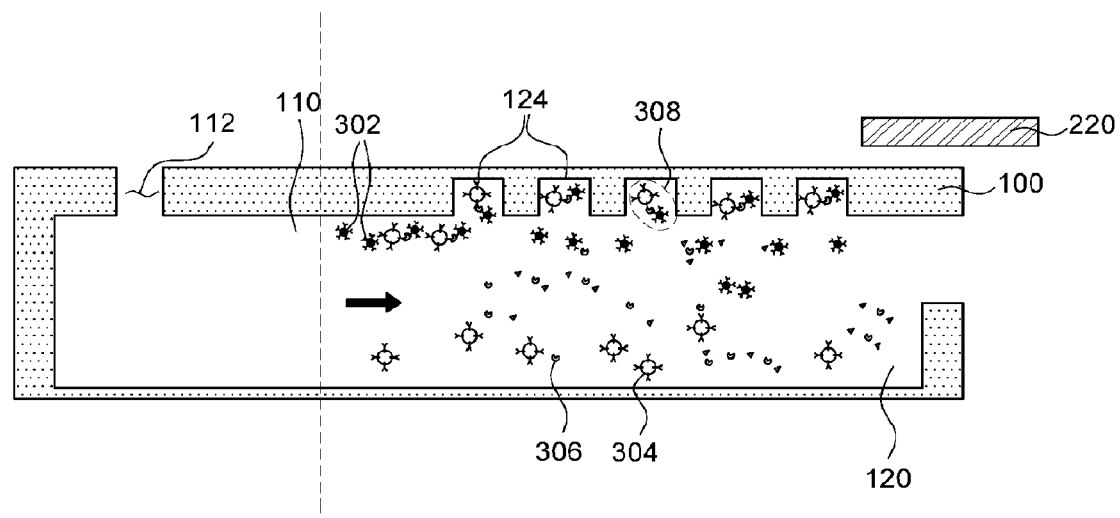
FIG. 3E exemplarily illustrates a detection channel in a microchip for quantitatively analyzing an antigen according to an embodiment of the present invention.

FIG. 3A illustrates a procedure of a method of quantitatively analyzing an antigen using a microchip and device for quantitatively analyzing an antigen according to an embodiment of the present invention. FIG. 3B exemplarily illustrates a step of mixing an assay sample, magnetic particles, and beads in a method of quantitatively analyzing an antigen. FIGS. 3C and 3D illustrate a schematic side view of a microchip for quantitatively analyzing an antigen according to an embodiment of the present invention and an enlarged view of a main part to describe a process of detecting a target antigen. FIG. 3E exemplarily illustrates a detection channel in a microchip for quantitatively analyzing an antigen according to an embodiment of the present invention.

Referring to FIGS. 3A and 3B, first, an assay sample including target antigens 306, magnetic particles 302 on which first antibodies for the target antigens 306 are immobilized, and beads 304 on which second antibodies for the target antigens 306 are immobilized are mixed (S310), for quantitative analysis of a target antigen. Here, the magnetic particles 302 and the beads 304 may be in the form of lyophilized powder, and the beads 304 may be transparent polystyrene beads. Further, the first and second antibodies may be respectively attached $1\times10^5$ to $4\times10^5$ times to the magnetic particles 302 and the beads 304. As a result of the mixing step (S310), an immune response may occur and asymmetric immune complexes 308 formed by coupling of the target antigens 306, the magnetic particles 302 and the beads 304 may be generated. Accordingly, a reaction sample 312 including the asymmetric immune complexes 308 may be prepared. Meanwhile, the reaction sample 312 may include the magnetic particles 302, the beads 304 and the target antigens 306 which have not been subjected to an immune response and, thus, are present in small amounts.

Referring to FIGS. 3A and 3C, the reaction sample 312 including the asymmetric immune complexes 308 generated in the mixing step (S310) is added dropwise through an inlet 112 formed in the microchip 100 for quantitatively analyzing an antigen, for quantitative analysis of the target antigens 306 (S320). As a result of the addition step (S320), the reaction sample 312 may be injected in a sufficient amount into the input channel 110.

Referring to FIGS. 3A and 3D, the microchip 100 for quantitative analysis is introduced into the device 200 for quantitative analysis including the magnetic force applicator 220 and the image sensor 230, and magnetism is applied near the detection channel 120 of the microchip 100 for quantitative analysis (S330). Here, the magnetic force applicator 220 may be disposed to correspond to a surface at which the wells 124 end on an upper surface of the detection channel 120 including the wells 124. More particularly, in the application step (S330), the immune complexes 308 in the added reaction sample 312 float at an upper part of the microchip 100 by magnetism applied by the magnetic particles 302. Further, the immune complexes 308 may rotate and move to the detection channel 120 by the magnetic force applicator 220.

Figure 3F:
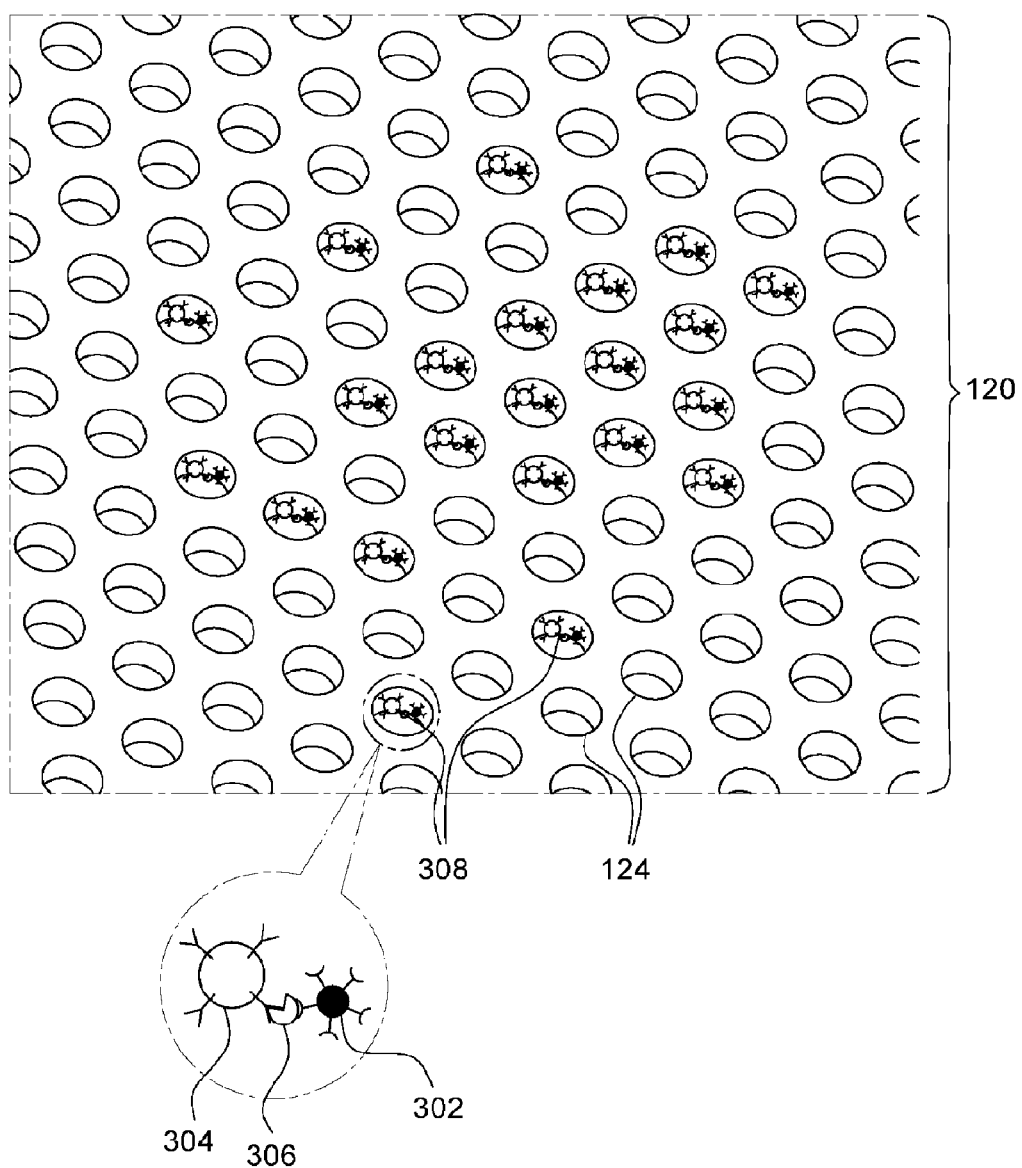
FIGS. 3F to 3I exemplarily illustrate a step of reconstructing shadow images of immune complexes acquired by an image sensor to count the number of target antigens, in a method of quantitatively analyzing an antigen.

Referring to FIGS. 3A and 3E, in the application step (S330), the immune complexes 308 having moved in one direction while rotating on an upper surface of the microchip 100 by magnetism may be captured in the plurality of wells 124 formed in the detection channel 120. Referring to FIG. 3F, as magnetism is applied by the magnetic force applicator 220, the immune complexes 308 including the magnetic particles 302 may be immobilized in the wells 124. Further, the aggregated asymmetric immune complexes 308 may be separated by the wells 124. As a result, one asymmetric immune complex 308 may be captured in one well 124. Meanwhile, the single magnetic particles 302 that do not form the asymmetric immune complexes 308 may also be captured in the wells 124. However, the magnetic particles 302 may have a size that cannot be detected by the image sensor 230. Further, the single beads 304 and single target antigens 306 that do not form the complexes 308 do not respond to magnetism, thereby exiting the detection channel 120 by the flow of a fluid.

Referring to FIG. 3A, using the image sensor 230 of the device for quantitatively analyzing an antigen, images of the asymmetric immune complexes 308 captured in the detection channel 120 or the detection parts 122 are acquired, and beads 304 with countable sizes in the asymmetric immune complexes 308 are detected, thereby indirectly counting the number of the target antigens 306 (S340). For example, in the counting step (S340), the processor 240 of the device for quantitatively analyzing an antigen may reconstruct a high-resolution image based on a plurality of low-resolution images of the asymmetric immune complexes 308 which are acquired through the image sensor 230, thereby being capable of counting the asymmetric immune complexes 308 in the high-resolution image. As a result, quantitative analysis for the target antigens 306 may be performed.

Hereinafter, a procedure of counting target antigens detected by the method of quantitatively analyzing an antigen according to an embodiment of the present invention is described in detail with reference to FIGS. 3G to 3I. Here, reference numerals used in FIGS. 1, 2, and 3A to 3F are used to refer to components for convenience of description.

Figure 3G:
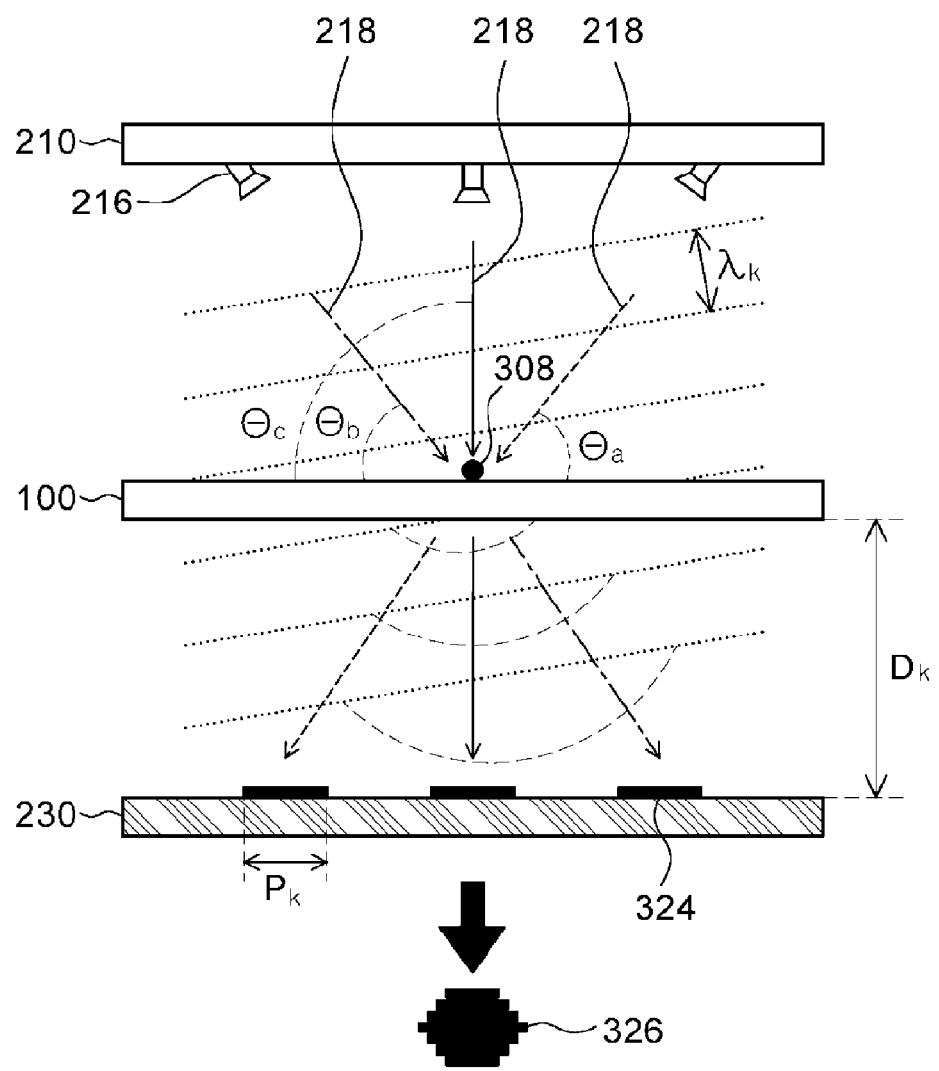
Figure 3H:
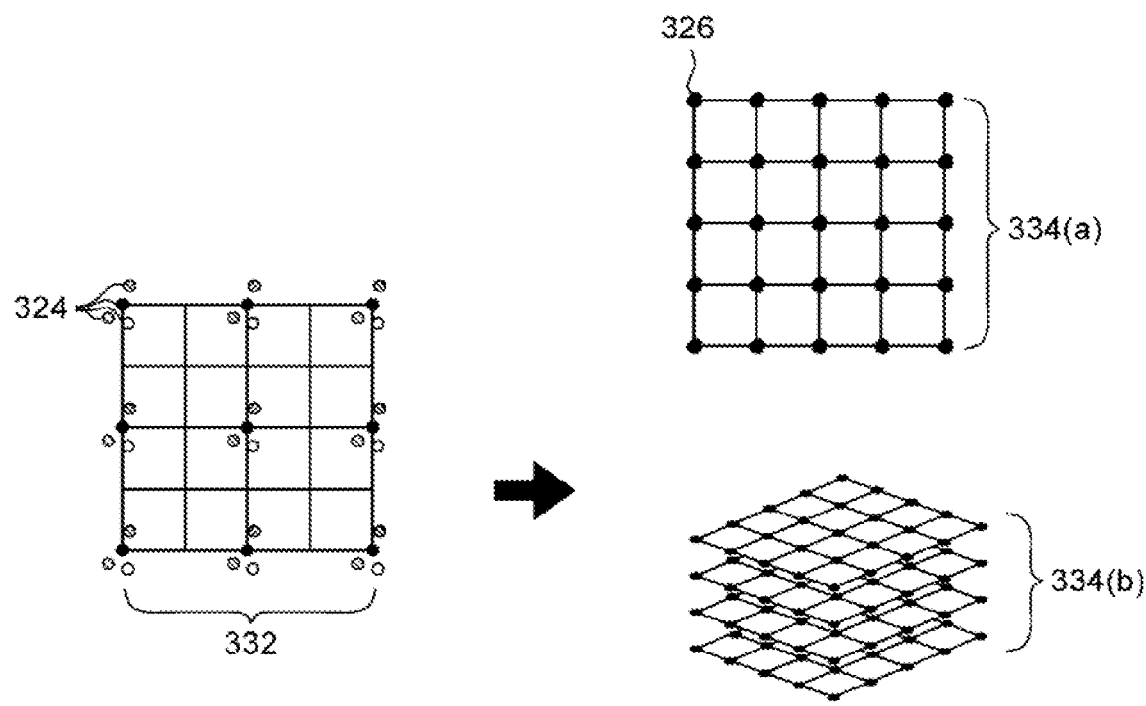
Figure 3I:
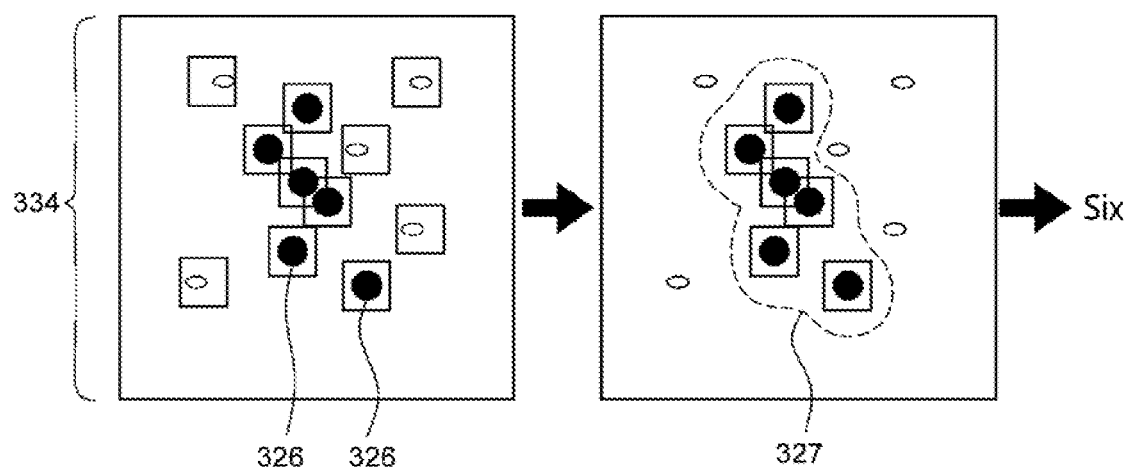

FIGS. 3G to 3I exemplarily illustrate a step of reconstructing shadow images of immune complexes acquired by an image sensor to count the number of target antigens, in a method of quantitatively analyzing an antigen.

Referring to FIGS. 3G and 3H, as the microchip 100 for quantitatively analyzing an antigen in which the immune complexes 304 are captured is irradiated with each of a plurality of LEDs 216 of the light irradiator 210 of the device for quantitatively analyzing an antigen, at a plurality of angles (θa, θb, θc), low-resolution images 332 including shadows 324 of the plurality of asymmetric immune complexes may be acquired.

Next, referring to FIG. 3H, a high-resolution image 334, which includes asymmetric immune complexes 326, reconstructed based on a pixel value (Pa) of each of the shadows 324 of the plurality of asymmetric immune complexes, the wavelengths (λk) of lights 218 radiated to different regions, a light emission angle (θa, θb, or θc) of each of a plurality of LEDs 216, and an interval (Dk) between the image sensor 230 and the microchip 100 for quantitatively analyzing an antigen (or the detection channel 120, the detection parts 122) may be acquired. Here, the high-resolution image 334 may consist of multilayer images of the asymmetric immune complexes 308 (see 334(a) and 334(b)).

Next, referring to FIG. 3I, the asymmetric immune complexes 308 may be counted based on the acquired high-resolution image 334. For example, the plurality of reconstructed asymmetric immune complexes 326 distributed in the detection parts 122 in the high-resolution image 334 recognized by an align key pattern may be matched with predetermined template. Next, a quantitative analysis result of the target antigens 306 may be obtained by counting the template-matched immune complexes 327, more particularly the beads 304.

Hereinafter, detection results of a target antigen in a microchip for quantitatively analyzing an antigen according to an embodiment of the present invention, dependent upon the concentration of a target antigen, are exemplarily described with reference to FIGS. 4A to 4C. Here, reference numerals used in FIG. 3A to FIG. 3F are used to refer to components for convenience of description.

Figure 4A:
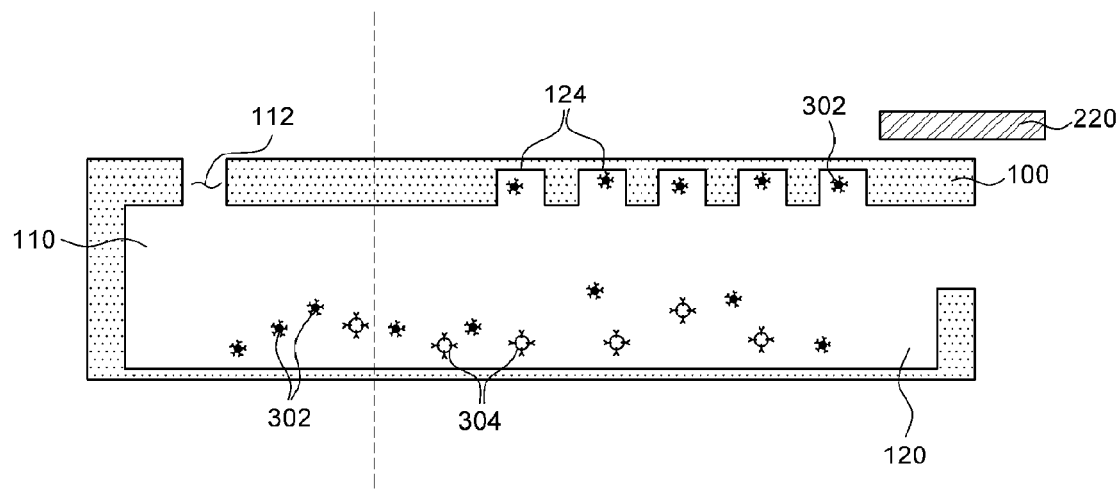
FIGS. 4A to 4C exemplarily illustrate a detection channel in a microchip for quantitatively analyzing an antigen, at different concentrations of a target antigen.
Figure 4B:
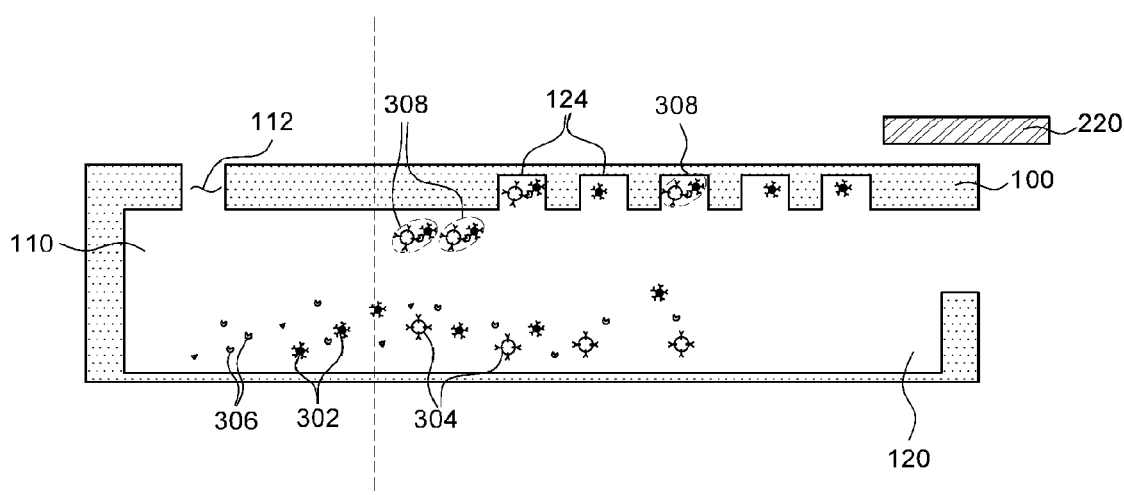
Figure 4C:
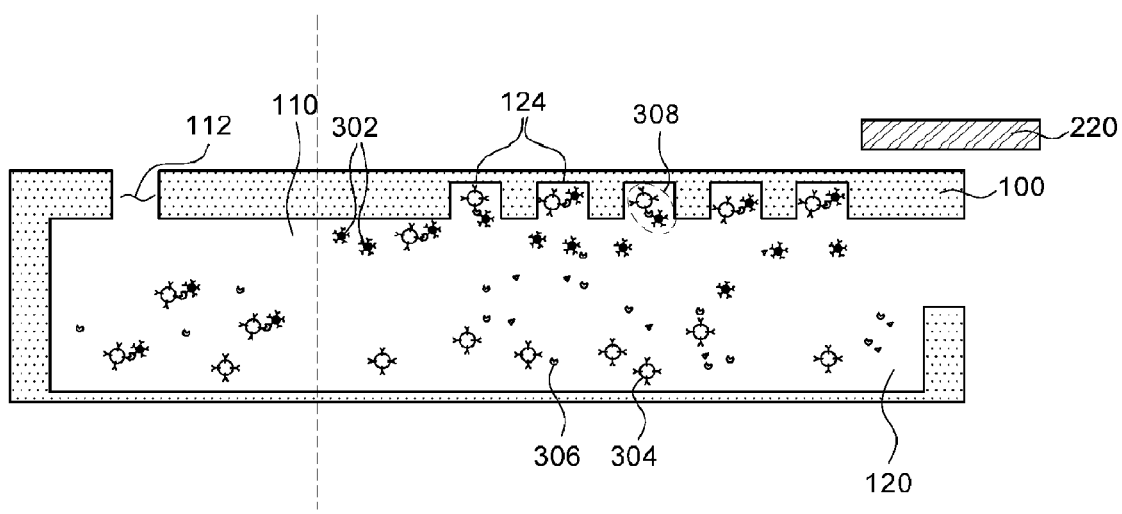

FIGS. 4A to 4C exemplarily illustrate a detection channel in a microchip for quantitatively analyzing an antigen, at different concentrations of a target antigen.

FIG. 4A illustrates the microchip 100 for quantitatively analyzing an antigen to which magnetism has been applied by the magnetic force applicator 220, when the reaction sample 312 excluding the target antigens 306 is introduced. More particularly, the magnetic particles 302 and the beads 304 cannot form the immune complexes 308 due to the absence of an antigen. As a result, magnetism is only applied to the magnetic particles 302 by the magnetic force applicator 220, so that the magnetic particles 302 may move to the detection channel 120 and may be captured and immobilized in the plurality of wells 124 in the detection channel 120.

FIG. 4B illustrates the microchip 100 for quantitatively analyzing an antigen to which magnetism has been applied by the magnetic force applicator 220, when the reaction sample 312 including the target antigens 306 at a low concentration is introduced. More particularly, the magnetic particles 302 and the beads 304 may form the immune complexes 308 by the target antigens 306. Here, the magnetic particles 302 in the immune complexes 308 may actively control the flow of the reaction sample 312 in the microchip 100 for quantitatively analyzing an antigen, and the beads 304 in the immune complexes 308 may be responsible for signaling such that immune complexes 308 can be counted. As magnetism is applied to the magnetic particles 302, the immune complexes 308 may move to the detection channel 120 and may be captured and immobilized in the plurality of wells 124 in the detection channel 120. Accordingly, the target antigens 306 at a low concentration may be effectively captured in the microchip 100 for quantitatively analyzing an antigen, and the target antigens 306 present at a low concentration may be quantitatively analyzed by counting the beads 304 with a countable size in the captured immune complexes 308.

FIG. 4C illustrates the microchip 100 for quantitatively analyzing an antigen to which magnetism has been applied by the magnetic force applicator 220, when the reaction sample 312 including the target antigens 306 at a high concentration is introduced. More particularly, the magnetic particles 302 and the beads 304 may form the immune complexes 308 together with the target antigens 306 at a high concentration and, as magnetism is applied, most of the immune complexes 308 may be captured and immobilized in the plurality of wells 124 in the detection channel 120. Accordingly, the target antigens 306 present at a high concentration may be highly accurately, quantitatively analyzed by counting the beads 304 with a countable size in the captured immune complexes 308.

EXAMPLE 1

Evaluation of Microchip and Device for Quantitatively Analyzing Antigen According to Embodiment of Present Invention and Method of Quantitatively Analyzing Antigen Using Microchip and Device Hereinafter, results of laboratory-level immune response experiments for a microchip and device for quantitatively analyzing an antigen according to an embodiment of the present invention and a method of quantitatively analyzing an antigen using the microchip and the device are described with reference to FIG. 5A.

For evaluation, magnetic particles having a particle diameter of 0.1 μm and beads having a particle diameter of 0.2 μm were used, and a nuclear protein of influenza A virus exhibiting an immune response to an antibody immobilized on the magnetic particles and an antibody immobilized on the beads was used as an antigen. Here, the magnetic particles were set to be green at a wavelength of 532 nm, and the beads were set to be red at a wavelength of 635 nm. A well plate containing the magnetic particles and the beads was treated with the antigen at each of concentrations of 0 pM, 0.1 pM, 10 pM, 100 pM and 1000 pM, shaking incubation was performed for 2 hours to induce an immune response, and the magnetic particles were washed three times. An absorbance of the washed plate was measured at 532 nm and 635 nm, and immune response results dependent upon antigen concentrations were confirmed.

Figure 5A:
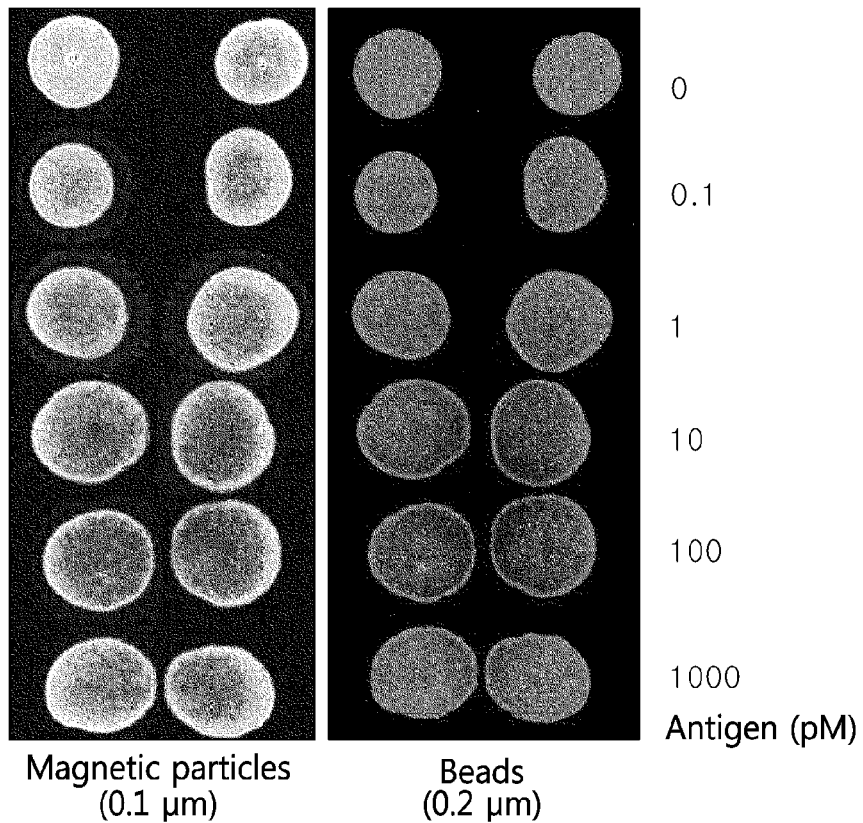
FIG. 5A illustrates results of laboratory-level immune response experiments to evaluate a microchip and device for quantitatively analyzing an antigen according to an embodiment of the present invention and a method of quantitatively analyzing an antigen using the microchip and the device.
Figure 5A:
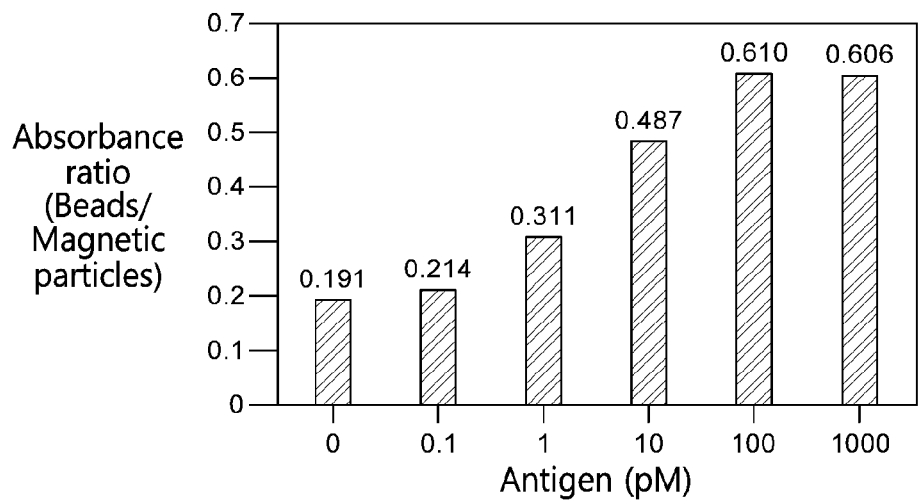

FIG. 5A illustrates results of laboratory-level immune response experiments to evaluate a microchip and device for quantitatively analyzing an antigen according to an embodiment of the present invention and a method of quantitatively analyzing an antigen using the microchip and the device.

FIG. 5A (a) illustrates absorbance measurement results. Here, an increase in signal intensity may mean an increase in an immune response. In particular, when the concentration of the antigen was 1 pM or higher, an immune response with the magnetic particles and the beads occurred. Further, when the antigen at a concentration of 100 pM was compared with the antigen at a concentration of 1000 pM, a significant difference in the immune responses was not observed.

Figure 5B:
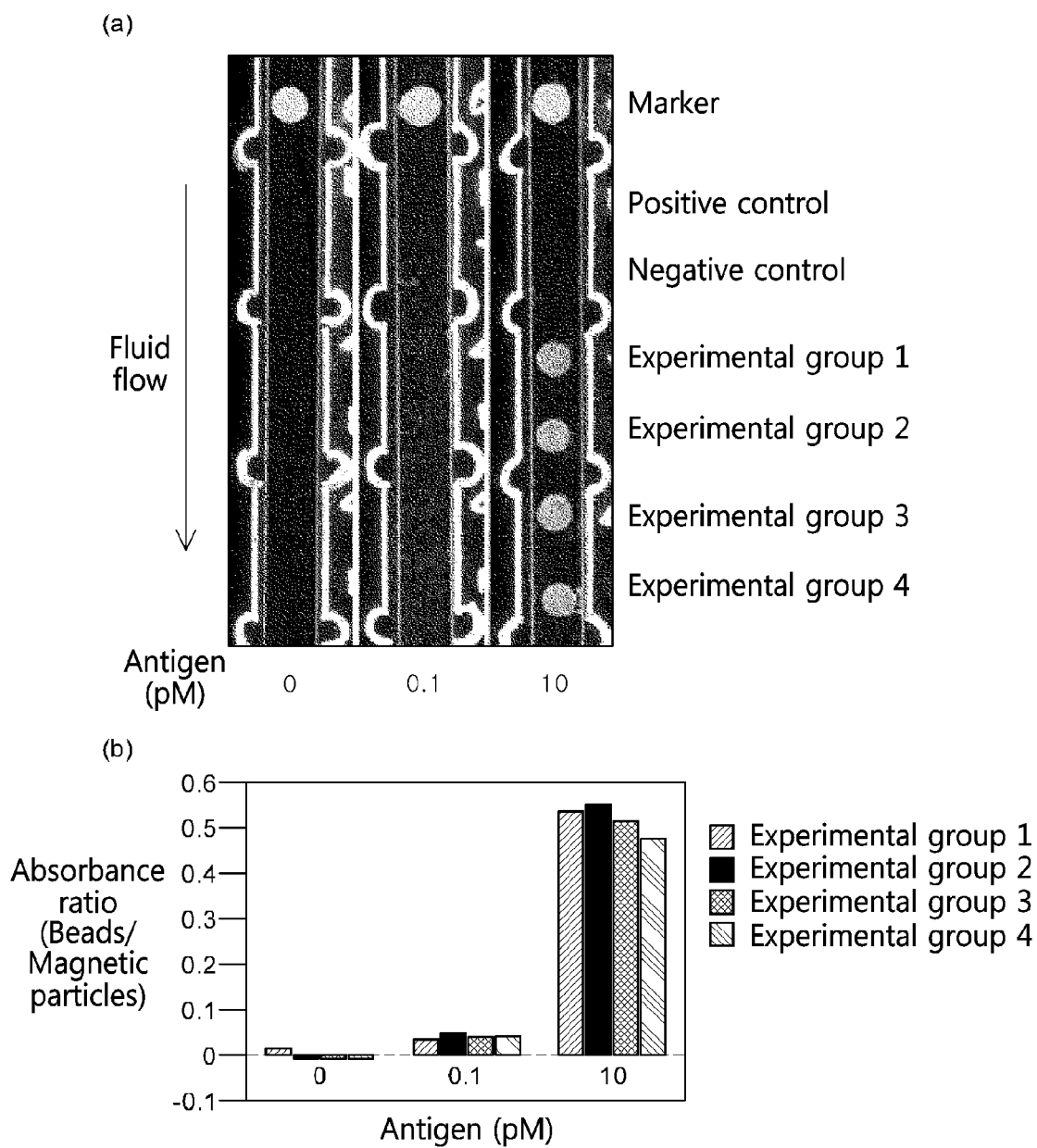
FIG. 5B illustrates experimental results of an immune response in a microchip to evaluate the reliability of a microchip and device for quantitatively analyzing an antigen according to an embodiment of the present invention and a method of quantitatively analyzing an antigen using the microchip and the device.

FIG. 5B (b) illustrates absorbance ratios of beads to magnetic particles, which represent signal values of the antigen, relative to a base signal. As shown in FIG. 5A (a), an absorbance ratio significantly increased to 0.311 when the concentration of the antigen was 1 pM or higher, which indicates that an immune response with the magnetic particles and the beads occurred. Further, absorbance ratios when respectively treated with the antigen at a concentration of 100 pM and the antigen at a concentration of 1000 pM were respectively 0.610 and 0.606 which are similar values. This may indicate that there is no significant immune response between the antigen at a concentration of 100 pM and the antigen at a concentration of 1000 pM.

As a result, the antigen at a concentration of 1 pM or higher may immunoreact with the magnetic particles and the beads, so that asymmetric immune complexes via the antigen may be formed. Accordingly, in the microchip and device for quantitatively analyzing an antigen according to an embodiment of the present invention and the method of quantitatively analyzing an antigen using the microchip and the device, an immune response of magnetic particles and beads via an antigen is used, so that a target antigen in asymmetric immune complexes may be detected and quantitatively analyzed. In addition, for efficient quantitative analysis, the concentration of a target antigen in an assay sample may be 1 pM to 100 pM.

Hereinafter, with reference to FIG. 5B, immune response experiments for the microchip for quantitatively analyzing an antigen according to an embodiment of the present invention are carried out to evaluate the reliability of a microchip and device for quantitatively analyzing an antigen according to an embodiment of the present invention and a method of quantitatively analyzing an antigen using the microchip and the device are described.

For evaluation, a nuclear protein of influenza virus A was used as an antigen. Further, M-2$^{nd}$ 555 immobilized on the detection channel of the microchip for quantitatively analyzing an antigen was used as a marker, EDC (1-ethyl-3-(3-dimethylamino-propyl) carbodiimide/NHS ((N-hydroxysuccinimide) used to immobilize an antibody on magnetic particles was used as a positive control, and thrombin was used as a negative control. In addition, for this evaluation, beads, an assay sample prepared by reacting the beads, the magnetic particles at 40 ng/μl (or magnetic particles at 100 ng/μl), and the antigen were introduced into the microchip for quantitatively analyzing an antigen, and an absorbance was measured on an upper or lower surface of the detection channel.

FIG. 5B illustrates experimental results of an immune response in a microchip to evaluate the reliability of a microchip and device for quantitatively analyzing an antigen according to an embodiment of the present invention and a method of quantitatively analyzing an antigen using the microchip and the device.

FIG. 5B(a) illustrates results of immune responses between the antigen, the magnetic particles and the beads which occur in the detection channel of the microchip for quantitatively analyzing an antigen with increased concentration of the antigen. More particularly, in Experimental Group 1 wherein the antigen, the beads and the magnetic particles at 40 ng/μl were reacted and an immune reaction was measured on the upper surface of the microchip for quantitatively analyzing an antigen, Experimental Group 2 wherein the antigen, the beads and the magnetic particles at 40 ng/μl were reacted and an immune reaction was measured on the lower surface of the microchip for quantitatively analyzing an antigen, Experimental Group 3 wherein the antigen, the beads and the magnetic particles at 100 ng/μl were reacted and an immune reaction was measured on the upper surface of the microchip for quantitatively analyzing an antigen, and Experimental Group 4 wherein the antigen, the beads and the magnetic particles at 100 ng/μl were reacted and an immune reaction was measured on the lower surface of the microchip for quantitatively analyzing an antigen, immune responses occurred in the antigen at concentrations of 0.1 nM and 10 nM. As a result, immune complexes were formed in the microchip for quantitatively analyzing an antigen.

FIG. 5B (b) illustrates an absorbance ratio of each of the experimental groups relative to a negative control. In particular, it was confirmed that, when the magnetic particles at concentrations of 40 ng/μl and 100 ng/μl were used at the same antigen concentration (0.1 nM or 10 nM), there was no significant difference. Further, the immune responses in the upper surface and the lower surface of the microchip for quantitatively analyzing an antigen did not exhibit a significant difference. However, with regard to the concentration of antigen, it was confirmed that the absorbance ratio increased with increasing antigen concentration. This result may indicate that use of the antigen at high concentrations may cause increased immune response and, further an increase in the number of immune complexes captured in the microchip for quantitatively analyzing an antigen.

As described above, immune complexes can be captured in the microchip for quantitatively analyzing an antigen, and the method of quantitatively analyzing an antigen using the microchip can provide a highly reliable analysis result.

Figure 5C:
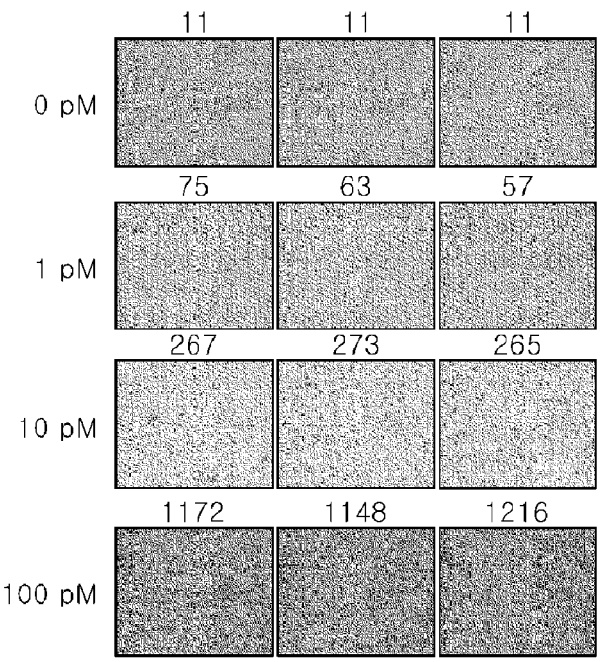
FIG. 5C illustrates quantitative analysis results of a target antigen, obtained using a microchip and device for quantitatively analyzing an antigen according to an embodiment of the present invention and a method of quantitatively analyzing an antigen using the microchip and the device.
Figure 5C:
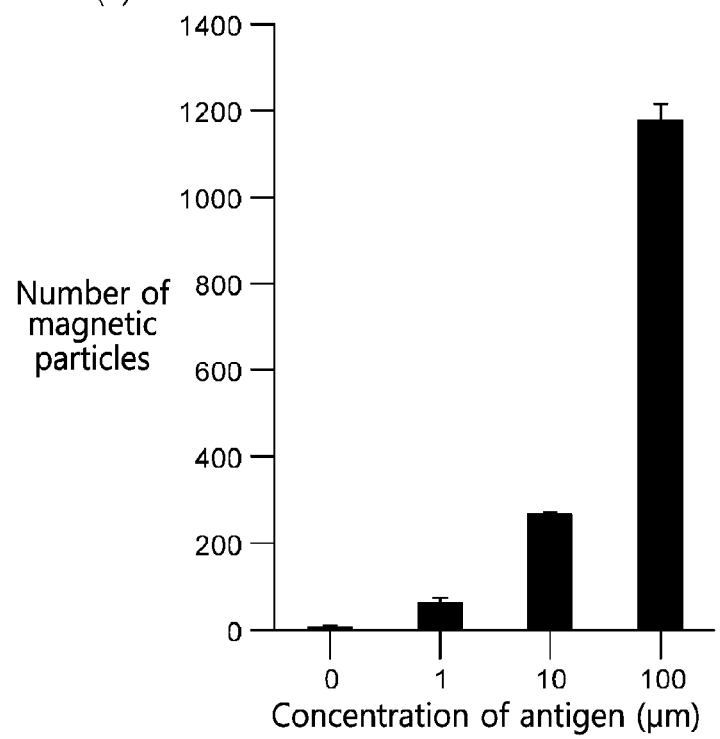

Hereinafter, FIG. 5C illustrates quantitative analysis results of the target antigen using the microchip and device for quantitatively analyzing an antigen according to an embodiment of the present invention and the method of quantitatively analyzing an antigen using the microchip and the device.

For the evaluation, a nuclear protein of influenza A virus was used as a detection target antigen, and experiments were carried out at four antigen concentrations. In particular, the four concentrations of the influenza A virus nuclear proteins used for the evaluation were 0 pM, 1 pM, 10 pM and 100 pM.

FIG. 5C illustrates quantitative analysis results of a target antigen, obtained using a microchip and device for quantitatively analyzing an antigen according to an embodiment of the present invention and a method of quantitatively analyzing an antigen using the microchip and the device.

FIG. 5C (a) illustrates some images of the detection channel of the microchip for quantitatively analyzing an antigen according to an embodiment of the present invention.

In the detection channel to which the influenza A virus nuclear protein was not added, 11 beads were observed for every 3 replicates. This result may indicate the number of beads captured in the detection channel by the flow of the fluid.

In the detection channels to which an assay sample prepared by immunoreacting the antigen at 1 pM with the beads and the magnetic particles was added, 75, 63, and 57 beads were observed for each repeated experiment. In addition, in the detection channels to which an assay sample prepared by immunoreacting the antigen at 10 pM with the beads and the magnetic particles was added, 267, 273 and 265 beads were observed for each repeated experiment. In addition, in the detection channels to which an assay sample prepared by immunoreacting the antigen at 100 pM with the beads and the magnetic particles was added, 1172, 1148 and 1216 beads were observed for each repeated experiment. Here, it was confirmed that the beads, more particularly the immune complexes, observed in the detection channels were captured in the wells in the detection channels.

FIG. 5C (b) is a graph illustrating the number of the magnetic particles dependent upon a concentration increase of the nuclear protein of influenza A virus. As a result, it was confirmed that the number of the magnetic particles increased in proportion to a concentration increase of the influenza A virus nuclear protein.

As shown in Example 1, by using the microchip and device for quantitatively analyzing an antigen according to an embodiment of the present invention and the method of quantitatively analyzing an antigen using the microchip and the device, a target antigen present in a trace amount of a pM unit in an assay sample can be highly sensitively detected.

In particular, the microchip for quantitatively analyzing an antigen according to an embodiment of the present invention and the method of quantitatively analyzing an antigen using the microchip three-dimensionally utilize particles that play two different roles to use immune complexes wherein an antibody is immobilized on a larger surface area relative to a volume, thereby being capable of increasing the efficiency of immune response. Accordingly, the present invention can effectively detect a target antigen and target substance at low concentrations.

Further, the microchip for quantitatively analyzing an antigen according to an embodiment of the present invention which is configured to balance fluid drag and magnetic force can provide a uniform movement pattern of an assay sample. As a result, the present invention can overcome drawbacks related to detection and analysis due to non-uniform fluid movement patterns of existing microchips for quantitatively analyzing an antigen.

Further, by using the microchip and device for quantitatively analyzing an antigen according to an embodiment of the present invention and the method of quantitatively analyzing an antigen using the microchip and the device, the number of beads can be optically counted without use of a fluorescence-labeled antibody, thereby providing quantitative analysis for a target antigen.

In addition, in the microchip and device for quantitatively analyzing an antigen according to an embodiment of the present invention and the method of quantitatively analyzing an antigen using the microchip and the device, simultaneous antigen analysis tests for a plurality of target antigens can be carried out by adjusting the sizes, shapes, and the like of beads for the plurality of target antigens to provide different complex shapes and analyzing patterns shown in a plurality of wells in which the target antigens are captured.

Although the embodiments of the present invention have been described in more detail with reference to the accompanying drawings, the present invention is not limited to the embodiments, and may be modified into various forms without departing from the technical spirit of the present invention. Thus, the embodiments disclosed in the present invention are not intended to limit the technical idea of the present invention but to describe the present invention, and the scope of the technical idea of the present invention is not limited by the embodiments. Therefore, it should be understood that the embodiments described above are exemplary in all respects and not restrictive. The protection scope of the present invention should be interpreted by the following claims, and all technical ideas within the equivalent scope should be interpreted as being included in the scope of the present invention.

DESCRIPTION OF SYMBOLS

100: microchip for quantitatively analyzing antigen
110: input channel
112: inlet
120: detection channel
122: detection parts
124: wells
130: flow retention channel
131: through holes
200: device for quantitatively analyzing antigen
210: light irradiator
212: pinhole aperture
214: light
216: LED
218: light irradiated to different regions
220: magnetic force applicator
230: image sensor
240: processor
302: magnetic particles
304: beads
306: target antigen
308: asymmetric immune complexes
312: reaction sample
324: shadows of asymmetric immune complex
326: reconstructed asymmetric immune complex
327: immune complexes matched with template
332: low-resolution image
334: high-resolution image
334(a): high-resolution plane image
334(b): high-resolution side image
S310: mix
S320: add dropwise
S330: apply electromagnetic force
S340: count number of target antigens

The invention claimed is:

1. A method of quantitatively analyzing an antigen, the method comprising:
mixing an assay sample comprising target antigens, magnetic particles and beads, wherein a first antibody subjected to an antigen-antibody reaction with a target antigen of the target antigens is immobilized, on each of the magnetic particles and a second antibody different from the first antibody is immobilized on each of the beads;
adding dropwise the mixed assay sample to a microchip for quantitatively analyzing an antigen;
introducing the microchip into a digital inline microscope-based detector comprising a magnetic force applicator and applying magnetism to the microchip using the magnetic force applicator; and
detecting the beads using images acquired in the detector to count the number of the target antigens,
wherein the microchip is configured to flow the assay sample to a detection channel formed inside the microchip to detect asymmetric immune complexes, and each of the asymmetric immune complexes is formed by coupling of a target antigen of the target antigens, a magnetic particle of the magnetic particles and a bead of the beads, and the detection channel comprises a plurality of wells formed on an upper or lower surface of the microchip,
wherein the applying of the magnetism comprises applying the magnetism to the microchip using the magnetic force applicator disposed at a position adjacent to the plurality of wells and the asymmetric immune complexes are captured in the plurality of wells by magnetic force,
wherein the detecting of the beads comprises:
acquiring, by an image sensor disposed below the lower surface of the microchip, a plurality of first images of an asymmetric immune complex of the asymmetric immune complexes captured in the plurality of wells by irradiating the asymmetric immune complex of the asymmetric immune complexes captured in the plurality of wells with light at a plurality of different emission angles using a plurality of light emitting elements of a light irradiator disposed above the upper surface of the microchip,
reconstructing a second image based on the acquired plurality of first images of the asymmetric immune complex of the asymmetric immune complexes, a resolution of the second image being higher than a resolution of each of the plurality of first images, and
counting the number of the beads based on the reconstructed second image,
wherein the second image is reconstructed based on a pixel value of each of shadows of the plurality of asymmetric immune complexes, wavelengths of lights radiated to different regions, a light emission angle of each of the plurality of light emitting elements of the light irradiator and an interval between the image sensor and the microchip for quantitatively analyzing an antigen,
wherein an objective lens is not disposed between the microchip and the image sensor,
wherein the shadows of the plurality of asymmetric immune complexes are formed at different locations on the image sensor by irradiating the asymmetric immune complex with light at the plurality of different emission angles using the plurality of the plurality of light emitting elements, and wherein the second image consists of multilayer images of the asymmetric immune complexes.

2. The method according to claim 1, wherein the detecting comprises counting the number of the asymmetric immune complexes captured in the plurality of wells during applying of the magnetism to the magnetic force applicator.

3. The method according to claim 1, wherein one asymmetric immune complex is immobilized in each of the plurality of wells, and the detecting comprises counting the wells, in each of which one asymmetric immune complex is captured.

4. The method according to claim 1, wherein each of the magnetic particles has a particle diameter of 0.05 to 2.8 μm, and each of the beads has a particle diameter of 0.5 to 5 μm.

5. The method according to claim 4, wherein the magnetic particles are not detected by the detector, and the beads are detected by the detector.

6. The method according to claim 1, wherein each of the first and second antibodies differs from a fluorescence-labeled antibody and is configured to bind to different epitopes of the same target antigen.

7. The method according to claim 1, wherein the first and second antibodies are attached in a number of $10^5$ times the square of a radius of a particle diameter of each of the magnetic particles and the beads.

8. The method according to claim 1, wherein the target antigens are in the assay sample at a concentration of 1 pM to 1000 pM.

* * * * *